US00RE39218E

(19) United States
(12) Reissued Patent
Mellul et al.

(10) Patent Number: US RE39,218 E
(45) Date of Reissued Patent: Aug. 1, 2006

(54) ANHYDROUS AND WATER-RESISTANT COSMETIC COMPOSITIONS

(75) Inventors: Myriam Mellul, L'Hay-les-Roses (FR); Paul Thau, Berkely Heights, NJ (US); Paul Fehn, Westfield, NJ (US); Carlos Pinzon, New Milford, NJ (US)

(73) Assignee: L'Oreal (FR)

(21) Appl. No.: 09/987,885

(22) Filed: Nov. 16, 2001

Related U.S. Patent Documents

Reissue of:
(64) Patent No.: 5,985,297
Issued: Nov. 16, 1999
Appl. No.: 09/138,379
Filed: Aug. 24, 1998

U.S. Applications:
(63) Continuation of application No. 08/882,298, filed on Jun. 25, 1997, now Pat. No. 5,849,316, which is a continuation of application No. 08/538,046, filed on Oct. 2, 1995, now abandoned.

(30) Foreign Application Priority Data

Sep. 30, 1994 (FR) ..... 94-11743

(51) Int. Cl.
*A61Q 1/04* (2006.01)
*A61Q 1/06* (2006.01)
*A61Q 1/12* (2006.01)
*A61Q 5/00* (2006.01)

(52) U.S. Cl. ..... 424/401; 424/59; 424/62; 424/70.1; 424/78.05; 514/844; 514/944

(58) Field of Classification Search ..... 424/401, 424/59, 62, 70.1, 78.03; 514/844, 944
See application file for complete search history.

(56) References Cited

U.S. PATENT DOCUMENTS

| | | | |
|---|---|---|---|
| 2,230,063 | A | 1/1941 | Klimist |
| 2,548,970 | A | 4/1951 | Grate |
| 2,566,722 | A | 9/1951 | Friedberg |
| 2,578,210 | A | 12/1951 | Silva |
| 2,676,182 | A | 4/1954 | Daudt et al. |
| 2,678,878 | A | 5/1954 | Stewart |
| 2,678,893 | A | 5/1954 | Kauppi |
| 2,681,878 | A | 6/1954 | Kauppi |
| 3,541,205 | A | 11/1970 | Hardigan et al. |
| 3,600,186 | A | 8/1971 | Mattson et al. |
| 3,642,635 | A | 2/1972 | MacLeod |
| 3,646,214 | A | 2/1972 | Katz |
| 3,836,647 | A | 9/1974 | Lange |
| 3,857,805 | A | 12/1974 | Prickril |
| 3,927,199 | A | 12/1975 | Micchelli et al. |
| 4,005,195 | A | 1/1977 | Jandacek |
| 4,005,196 | A | 1/1977 | Jandacek et al. |
| 4,119,712 | A | 10/1978 | Goldner et al. |
| 4,192,861 | A | 3/1980 | Micchelli et al. |
| 4,283,384 | A | 8/1981 | Jacquet et al. |
| 4,315,910 | A | 2/1982 | Nowak, Jr. et al. |
| 4,409,203 | A | 10/1983 | Gordon et al. |
| 4,421,769 | A | 12/1983 | Dixon et al. |
| 4,421,881 | A | 12/1983 | Benkendorf et al. |
| 4,425,364 | A | 1/1984 | Vanlerberghe et al. |
| 4,431,673 | A | 2/1984 | Goldner et al. |
| 4,486,405 | A | 12/1984 | Klein |
| 4,515,784 | A | 5/1985 | Bogardus et al. |
| 4,534,961 | A | 8/1985 | Liff |
| 4,574,082 | A | 3/1986 | Tietjen et al. |
| 4,578,266 | A | 3/1986 | Tietjen et al. |
| 4,601,757 | A | 7/1986 | Brown et al. |
| 4,649,045 | A | 3/1987 | Gaske et al. |
| 4,673,570 | A | 6/1987 | Soldati |
| 4,678,663 | A | 7/1987 | Scott et al. |
| 4,699,780 | A | 10/1987 | Jennings et al. |
| 4,725,495 | A | 2/1988 | Garbe et al. |
| 4,725,658 | A | 2/1988 | Thayer et al. |
| 4,747,419 | A | 5/1988 | Flynn et al. |
| 4,777,041 | A | 10/1988 | Mercado |
| 4,792,444 | A | 12/1988 | Fukasawa et al. |
| 4,795,631 | A | 1/1989 | Sheehan |
| 4,797,272 | A | 1/1989 | Linn et al. |
| 4,800,076 | A | 1/1989 | Bhat et al. |
| 4,801,447 | A | 1/1989 | Gum |
| 4,803,067 | A | 2/1989 | Brunetta et al. |
| 4,826,828 | A | 5/1989 | Wilmott et al. |
| 4,837,011 | A | 6/1989 | Macchio et al. |
| 4,839,163 | A | 6/1989 | Busch, Jr. |

(Continued)

FOREIGN PATENT DOCUMENTS

| | | | |
|---|---|---|---|
| DE | 3744352 | A1 | 7/1989 |
| DE | 3837473 | A1 | 5/1990 |
| DE | 4025040 | A1 | 2/1991 |
| EP | 0005922 | A1 | 12/1979 |
| EP | 0133963 | A2 | 3/1985 |
| EP | 0133963 | * | 3/1985 |
| EP | 0151984 | A2 | 8/1985 |

(Continued)

OTHER PUBLICATIONS

Derwent Abstract of FR–A–2688134.*
Arndt Schlosser et al., "Resins: The Other Kind of Silicones", Cosmetics & Toiletries Magazine, vol. 118, No. 8, Aug. 2003.
Harry's Cosmeticology, pp. 332–333 (Coloured Make–up Preparation), 7th Ed., Chemical Publishing Co., 1982.
Amphomer—Polymer for Hard Holding Hair Fixative Formulations; National Starch and Chemical Company, Specialty Polymers.
Leo, A.J., "Methods of Calculating Partition Coefficients", *Comprehensive Medicinal Chemistry*, (Eds., Hansch, Sammens, Taylor and Ransden), vol. 4, pp. 295–319, 1990.

(Continued)

*Primary Examiner*—Jyothsna Venkat
(74) *Attorney, Agent, or Firm*—Finnegan, Henderson, Farabow, Garrett & Dunner LLP

(57) ABSTRACT

An anhydrous, water-resistant cosmetic composition comprising silicone-containing materials, fillers and pigments. This composition may be used as a make-up product or as a hair product.

24 Claims, No Drawings

U.S. PATENT DOCUMENTS

| | | | | |
|---|---|---|---|---|
| 4,855,129 | A | | 8/1989 | Steinbach et al. |
| 4,873,078 | A | | 10/1989 | Edmundson et al. |
| 4,888,363 | A | | 12/1989 | Dulak et al. |
| 4,897,261 | A | | 1/1990 | Yamazaki et al. |
| 4,904,698 | A | | 2/1990 | Adkins, Jr. et al. |
| 4,935,228 | A | | 6/1990 | Finkenauer et al. |
| 4,946,302 | A | | 8/1990 | Uchida |
| 4,950,468 | A | | 8/1990 | Nakamura et al. |
| 4,954,532 | A | | 9/1990 | Elliott et al. |
| 4,966,933 | A | | 10/1990 | Kawakami et al. |
| 4,980,167 | A | | 12/1990 | Harashima et al. |
| 4,983,388 | A | | 1/1991 | Kuwata et al. |
| 4,988,503 | A | | 1/1991 | Macchio et al. |
| 4,992,477 | A | | 2/1991 | Geria |
| 4,994,264 | A | | 2/1991 | Verdon et al. |
| 4,996,239 | A | | 2/1991 | Matravers |
| 5,002,762 | A | | 3/1991 | Bolich, Jr. |
| 5,011,680 | A | | 4/1991 | Suzuki et al. |
| 5,013,763 | A | | 5/1991 | Tubesing et al. |
| 5,015,469 | A | | 5/1991 | Yoneyama et al. |
| 5,023,075 | A | | 6/1991 | Macchio et al. |
| 5,036,108 | A | | 7/1991 | Asahi et al. |
| 5,045,309 | A | | 9/1991 | Dell'Aquila |
| 5,051,489 | A | | 9/1991 | O'Lenick, Jr. |
| 5,053,221 | A | | 10/1991 | Robertson et al. |
| 5,061,481 | A | | 10/1991 | Suzuki et al. |
| 5,063,057 | A | | 11/1991 | Spellman et al. |
| 5,073,364 | A | | 12/1991 | Giezendanner et al. |
| 5,073,372 | A | | 12/1991 | Turner et al. |
| 5,085,855 | A | | 2/1992 | Shore |
| 5,085,856 | A | | 2/1992 | Dunphy et al. |
| 5,089,256 | A | | 2/1992 | Scheller et al. |
| 5,093,108 | A | | 3/1992 | Pappas et al. |
| 5,093,111 | A | | 3/1992 | Baker et al. |
| 5,104,586 | A | | 4/1992 | Brand et al. |
| 5,106,609 | A | | 4/1992 | Bolich, Jr. et al. |
| 5,106,611 | A | | 4/1992 | Forestier et al. |
| 5,106,625 | A | | 4/1992 | Yamamoto et al. |
| 5,108,736 | A | | 4/1992 | Schlossman |
| 5,118,496 | A | | 6/1992 | Herstein |
| 5,118,507 | A | | 6/1992 | Clement |
| 5,126,126 | A | | 6/1992 | Varaprath et al. |
| 5,141,741 | A | | 8/1992 | Isida et al. |
| 5,143,722 | A | | 9/1992 | Hollenberg et al. |
| 5,143,723 | A | | 9/1992 | Calvo et al. |
| 5,158,772 | A | | 10/1992 | Davis |
| 5,160,738 | A | | 11/1992 | Macaulay et al. |
| 5,183,588 | A | | 2/1993 | Salerno et al. |
| 5,183,589 | A | | 2/1993 | Brunetta et al. |
| 5,196,187 | A | | 3/1993 | Nicoll et al. |
| 5,206,012 | A | | 4/1993 | Farer et al. |
| 5,208,012 | A | | 5/1993 | Sudo et al. |
| 5,210,251 | A | | 5/1993 | Ohashi et al. |
| 5,213,716 | A | | 5/1993 | Patel et al. |
| 5,213,799 | A | | 5/1993 | Göring et al. |
| 5,216,033 | A | | 6/1993 | Pereira et al. |
| 5,219,560 | A | | 6/1993 | Suzuki et al. |
| 5,223,559 | A | | 6/1993 | Arraudeau et al. |
| 5,225,186 | A | | 7/1993 | Castrogiovanni et al. |
| 5,234,682 | A | | 8/1993 | Macchio et al. |
| 5,238,678 | A | | 8/1993 | Shiozawa et al. |
| 5,246,780 | A | | 9/1993 | Ferer et al. |
| 5,260,401 | A | | 11/1993 | O'Lenick, Jr. |
| 5,262,087 | A | | 11/1993 | Tachibana et al. |
| 5,266,321 | A | | 11/1993 | Shukuzaki et al. |
| 5,268,175 | A | | 12/1993 | Bombardelli et al. |
| 5,271,934 | A | | 12/1993 | Goldberg et al. |
| 5,283,062 | A | | 2/1994 | Elliott et al. |
| 5,288,482 | A | | 2/1994 | Krzysik |
| 5,288,493 | A | | 2/1994 | Martino et al. |
| 5,292,530 | A | | 3/1994 | McCrea et al. |
| 5,302,380 | A | | 4/1994 | Castrogiovanni et al. |
| 5,302,382 | A | | 4/1994 | Kasprzak |
| 5,304,325 | A | | 4/1994 | Kaufmann et al. |
| 5,306,498 | A | | 4/1994 | Vesperini et al. |
| 5,310,547 | A | | 5/1994 | Dunphy et al. |
| 5,312,968 | A | | 5/1994 | O'Lenick, Jr. et al. |
| 5,318,775 | A | | 6/1994 | Shore et al. |
| 5,324,506 | A | | 6/1994 | Calvo et al. |
| 5,328,683 | A | | 7/1994 | Harashima |
| 5,330,747 | A | | 7/1994 | Krzysik |
| 5,334,372 | A | | 8/1994 | Kawamata et al. |
| 5,338,536 | A | | 8/1994 | Thimineur et al. |
| 5,340,569 | A | | 8/1994 | Elliott et al. |
| 5,346,642 | A | | 9/1994 | Patel et al. |
| 5,362,482 | A | | 11/1994 | Yoneyama et al. |
| 5,364,325 | A | | 11/1994 | Matthews |
| 5,364,633 | A | | 11/1994 | Hill et al. |
| 5,368,848 | A | | 11/1994 | Brazinsky et al. |
| 5,380,527 | A | | 1/1995 | Legrow et al. |
| 5,382,433 | A | | 1/1995 | Pahlck et al. |
| 5,385,730 | A | | 1/1995 | Ichinohe |
| 5,387,417 | A | | 2/1995 | Rentsch |
| 5,389,365 | A | | 2/1995 | LeGrow et al. |
| 5,393,526 | A | | 2/1995 | Castro |
| 5,397,566 | A | | 3/1995 | Thimineur et al. |
| 5,412,004 | A | | 5/1995 | Tachibana et al. |
| 5,413,792 | A | | 5/1995 | Ninomiya et al. |
| 5,417,967 | A | | 5/1995 | Kawamata et al. |
| 5,430,082 | A | | 7/1995 | Bentz |
| 5,446,114 | A | | 8/1995 | O'Lenick, Jr. |
| 5,451,610 | A | | 9/1995 | Krzysik |
| 5,462,737 | A | | 10/1995 | Pfleuger |
| 5,466,457 | A | | 11/1995 | Schneider et al. |
| 5,478,552 | A | | 12/1995 | Hasegawa |
| 5,486,355 | A | | 1/1996 | Berschied, Jr. |
| 5,488,121 | A | | 1/1996 | O'Lenick, Jr. |
| 5,494,938 | A | | 2/1996 | Kawa et al. |
| 5,496,544 | A | * | 3/1996 | Mellul et al. ..... 428/78.03 |
| 5,500,138 | A | | 3/1996 | Bacon et al. |
| 5,500,154 | A | | 3/1996 | Bacon et al. |
| 5,505,937 | A | | 4/1996 | Castrogiovanni et al. |
| 5,512,272 | A | | 4/1996 | Krzysik |
| 5,589,165 | A | | 12/1996 | Yoshida et al. |
| 5,648,066 | A | | 7/1997 | Stepniewski |
| 5,665,364 | A | | 9/1997 | McAtee et al. |
| 5,725,845 | A | | 3/1998 | Krog et al. |
| 5,738,841 | A | | 4/1998 | Mellul et al. |
| 5,747,017 | A | | 5/1998 | Nichols et al. |
| 5,800,816 | A | | 9/1998 | Brieva et al. |
| 5,837,223 | A | | 11/1998 | Barone et al. |
| 5,849,316 | A | * | 12/1998 | Mellul et al. ..... 424/401 |
| 5,902,592 | A | | 5/1999 | Bara et al. |
| 5,911,974 | A | | 6/1999 | Brieva et al. |
| 5,925,337 | A | | 7/1999 | Arraudeau et al. |
| 5,965,112 | A | | 10/1999 | Brieva et al. |
| 5,985,298 | A | | 11/1999 | Brieva et al. |
| 6,001,374 | A | | 12/1999 | Nichols |
| 6,010,709 | A | | 1/2000 | Nichols |
| 6,019,962 | A | | 2/2000 | Rabe et al. |
| 6,027,739 | A | | 2/2000 | Nichols |
| 6,036,947 | A | | 3/2000 | Barone et al. |
| 6,071,503 | A | | 6/2000 | Dreschsler et al. |
| 6,074,654 | A | | 6/2000 | Dreschsler et al. |
| 6,139,823 | A | | 10/2000 | Dreschsler et al. |
| 6,203,809 | B1 | | 3/2001 | Nichols |
| 6,274,152 | B1 | | 8/2001 | Brieva et al. |
| 6,395,263 | B1 | | 5/2002 | Nichols et al. |
| 6,464,964 | B1 | | 10/2002 | Brieva et al. |
| 6,509,009 | B1 | | 1/2003 | Nichols et al. |
| 6,562,322 | B1 | | 5/2003 | Brieva et al. |

FOREIGN PATENT DOCUMENTS

| | | | | |
|---|---|---|---|---|
| EP | 0179416 | A2 | | 4/1986 |
| EP | 0200839 | A1 | | 11/1986 |
| EP | 0205961 | A2 | | 12/1986 |
| EP | 0272832 | A2 | | 6/1988 |
| EP | 0 381 166 | A2 | | 8/1990 |
| EP | 0381166 | A2 | | 8/1990 |
| EP | 0381376 | A3 | | 8/1990 |
| EP | 0381376 | A2 | | 8/1990 |
| EP | 0 388 582 | A2 | | 9/1990 |
| EP | 0504966 | A1 | | 9/1992 |
| EP | 0515195 | A1 | | 11/1992 |
| EP | 0519727 | A1 | | 12/1992 |
| EP | 0521647 | | * | 1/1993 |
| EP | 0548694 | | * | 6/1993 |
| EP | 0590192 | A1 | | 4/1994 |
| EP | 0 590 192 | A1 | | 4/1994 |
| EP | 0602905 | A2 | | 6/1994 |
| EP | 0602905 | A3 | | 6/1994 |
| EP | 0610026 | A1 | | 8/1994 |
| EP | 0709083 | A2 | | 5/1996 |
| EP | 0748622 | A1 | | 12/1996 |
| FR | 2556940 | A1 | | 6/1985 |
| FR | 2638636 | A1 | | 5/1990 |
| FR | 2688134 | | * | 9/1993 |
| FR | 2707485 | A1 | | 1/1995 |
| GB | 1476194 | | | 6/1977 |
| GB | 1476195 | | | 6/1977 |
| GB | 2027341 | A | | 2/1980 |
| GB | 1569009 | | | 6/1980 |
| GB | 2107186 | A | | 4/1983 |
| GB | 2197783 | A | | 6/1988 |
| GB | 2197783 | B | | 6/1988 |
| GB | 2198037 | A | | 6/1988 |
| GB | 2211081 | A | | 6/1989 |
| GB | 2211081 | B | | 6/1989 |
| GB | 2274585 | A | | 8/1994 |
| GB | 2294392 | | | 5/1995 |
| JP | 55-028906 | | | 2/1980 |
| JP | 59-172495 | A | | 9/1984 |
| JP | SHO 61-65809 | | | 4/1986 |
| JP | 61-65809 | A | | 4/1986 |
| JP | SHO 61-158913 | | | 7/1986 |
| JP | 61-161211 | | | 7/1986 |
| JP | SHO 62-298512 | | | 12/1987 |
| JP | 63-230618 | | | 9/1988 |
| JP | 04-045155 | | | 2/1992 |
| JP | 05-065212 | | | 3/1993 |
| JP | 05-221829 | | | 8/1993 |
| JP | 06-024932 | | | 2/1994 |
| JP | 06-024933 | | | 2/1994 |
| JP | 06-072085 | | | 3/1994 |
| JP | 06-107518 | | | 4/1994 |
| JP | 06-118708 | | | 4/1994 |
| JP | 06166611 | A | | 6/1994 |
| JP | 07-267820 | | | 10/1995 |
| JP | 08-26936 | | | 1/1996 |
| JP | 08-81335 | | | 3/1996 |
| JP | 08-092034 | | | 4/1996 |
| JP | 08-092036 | | | 4/1996 |
| WO | WO 86/02001 | | | 4/1986 |
| WO | WO 91/08733 | | | 6/1991 |
| WO | WO 92/19215 | | | 11/1992 |
| WO | WO 96/19185 | | | 6/1996 |
| WO | WO 96/40044 | | | 12/1996 |
| WO | WO 97/01321 | | | 1/1997 |
| WO | WO 97/17057 | | | 5/1997 |
| WO | WO 97/17058 | | | 5/1997 |

OTHER PUBLICATIONS

Mark, J.E., *Physical Properties of Polymers Handbook*, AIP Press., Amer. Inst. Of Physics, Chap. 16, pp. 227–239.
Vaughan, C.D., "Solubility Effects in Product, Package, Penetration and Preservation", *Cosmetics & Toiletries*, vol. 103, pp. 47–69, 1988.
General Electric, GE Silicones, Patent Technology, 7 pp.
General Electric, GE Silicones, Preliminary Data Sheet, 4 pp.
Abstract: JP 63230618, Sep. 27, 1988.
Abstract: JP 6107518, Apr. 19, 1994.
Abstract: JP 55028906, Feb. 29, 1980.
Abstract: JP 62298512, Dec. 12, 1987.
WP Index 84–210426, Abstract JP 59122415.
Von Nostrand Reinhold Co., "*Hawleys Condensed Chemical Dictionary*," (Richard J. Lewis, Sr. res. 12$^{th}$ ed.), 1993, p. 635.
McGraw–Hil Book Co., "*McGraw–Hill Dictionary of Chemistry*", (Sybil P. Parker ed.), 1984, p. 319.
The Cosmetic, Toiletry and Fragrance Association, "CTFA Ingredient Handbook," (John A. Wenninger 7 G.N. McEwen, Jr. eds.) 1988, p. 213.
Al Disapio and Petrina Fridd, "*Silicones: use of substantive properties on skin and hair*", International Journal of Cosmetic Science, 10, 1988, pp. 75–89.
Skin Care by Dow Corning, Formulary of Product Applications, 1981.
Japanese Patent Abstract JP 59122415 Jul. 1984.
Dow Corning Corporation—Material Safety Data Sheet Jun. 1994.
International Cosmetic Ingredient Dictionary and Handbook, vol. 1, p. 1434.
English language Derwent Abstract of DE 1 913 569.
English language Derwent Abstract of EP 0 255 655 A2.
European Patent Office abstract and family listing of EP 0 255 655 A2.
English language Derwent Abstract of EP 0 268 950 A2.
European Patent Office abstract and family listing of EP 0 268 950 A2.
English language Derwent Abstract of FR 2 556 940 A.
English translation of JP 60–255714 A.
English translation of JP 61–161211 A.
English language abstract of JP 62–061911 A from Patent Abstracts of Japan.
English translation of JP 62–238212 A.
English translation of JP 62–298512 A.
English translation of JP 63–183516 A.
English translation of JP 01–143816 A.
English translation of JP 01–168607 A.
English translation of JP 01–250307 A.
English translation of JP 01–283209 A.
English translation of JP 05–32527 A.
English translation of JP 06–24932 A.
English translation of JP 07–258030 A.
English language Derwent Abstract of WO 91/12793 A1.
European Patent Office abstract and family listing of WO 91/12793 A1.
English language Derwent Abstract of WO 93/17660 A1.
European Patent Office abstract and family listing of WO 93/17660 A1.
English translation of CH 317302.
English translation of DE 1 012 730.
English translation of DE 967 031.
English translation of DE 1 018 194.

English translation of DE 968 535.
English translation of FR 1 301 966.
English language abstract of JP 59–172495 A from Patent Abstracts of Japan.
English language abstract of JP 61–65809 A from Patent Abstracts of Japan.
English language abstract of JP 07–267820 A from Patent Abstracts of Japan.
English language abstract of JP 08–26936 A from Patent Abstracts of Japan.
English language abstract of JP 08–81335 A from Patent Abstracts of Japan.
Origins Sunny Disposition, product labeling, Oct. 1993.

* cited by examiner

ANHYDROUS AND WATER-RESISTANT COSMETIC COMPOSITIONS

Matter enclosed in heavy brackets [ ] appears in the original patent but forms no part of this reissue specification; matter printed in italics indicates the additions made by reissue.

This is a continuation of application Ser. No. 08/882,298, filed Jun. 25, 1997 now U.S. Pat. No. 5,849,316, which is a continuation of application Ser. No. 08/538,046, filed Oct. 2, 1995, now abandoned.

The invention is directed to anhydrous and water-resistant make-up compositions comprising, inter alia, at least one silicone gum.

Water-resistant compositions in water-in-oil or water-in-silicone emulsion form are known in the prior art. The use of such emulsions relies on the fact that after spreading, the water evaporates and the oil or the silicone remains in contact with the skin, giving a water-resistant make-up. However, the application of such compositions has the drawback of leaving the skin with an oily appearance and of giving a greasy feel. The result obtained after application is not really natural, and the make-up shines or becomes shiny.

Another form of water-resistant cosmetic compositions is a composition in which fillers, including pigments, are introduced into a volatile or non-volatile silicone oil. The major drawback of this type of composition lies in the stretching effect on the skin, and in the unpleasant, dry sensation which appears after application. Furthermore, the effect sought in the use of such compositions containing pigments, namely a coloration of the skin, is often not achieved. The very nature of the composition is such that the distribution of the pigments in the composition after spreading is not homogeneous; the pigments spread more or less uniformly and tend to agglomerate in the pores and the folds in the skin. This effect runs counter to the search for a coloration close to that obtained naturally.

In all cases, the compositions obtained have faults both with regard to the stability and with regard to the homogeneity of the dispersion of the pigments. Solutions to these problems have been proposed, such as, for example, the use of water-soluble dyes or of dihydroxyacetone (DHA). In the case of water-soluble dyes, the make-ups obtained are not water-resistant and are not perfectly homogeneous.

Products using DHA are difficult to formulate, on account of the degradation and the incompatibility of DHA with many components usually used in compositions of this type. In addition, a major drawback of DHA, in its use in cosmetic compositions, lies in the development of unpleasant odors during ageing.

An object of the present invention is to provide solutions to the various problems encountered in the applications of the prior art and to propose a cosmetic composition possessing good water resistance and at the same time possessing good cosmetic properties.

The Inventors have been able to show, surprisingly and unexpectedly, that it is possible to obtain anhydrous, water-resistant make-up compositions which are highly homogeneous in particular with regard to spreading, by mixing together pigments and at least a large proportion of silicone gum and a silicone oil.

More particularly, a subject of the present invention is an anhydrous, water-resistant cosmetic composition preferably comprising from 2 to 50% of at least one silicone gum, from 10 to 90% of at least one silicone oil, from 0.5 to 15% of at least one pigment and from 0 to 30% of at least one filler.

The compositions according to the invention have the advantage of being stable over time. They are water-resistant since they are anhydrous, and do not contain any water-soluble dyes or solvent. They also have good staying power and do not cause any pulling effect on the skin.

It has furthermore been observed, surprisingly, that the pigments present in the compositions according to the invention were dispersed therein in an unexpectedly very homogeneous manner. This thus has the additional advantage of giving a very uniform and very homogeneous make-up of the skin.

In the following text, the percentages will always be given by weight of active material relative to the total weight of the composition.

In the compositions according to the invention, the silicone gum is preferably present in a proportion ranging from 2% to 50%, more preferably ranging from 4 to 15% and still more preferably ranging from 6% to 9%.

The silicone gum preferably has a molecular weight not greater than 1,500,000. More preferably, the silicone gum has a molecular weight ranging from 200,000 to 1,000,000.

The silicon gum preferably corresponds to the formula:

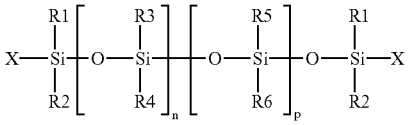

in which:

R1, R2, R5, and R6 each independently represents an alkyl radical having from 1 to 6 carbon atoms;

R3 and R4 each independently represents an alkyl radical having from 1 to 6 carbon atoms or an aryl radical;

X represents an alkyl radical having from 1 to 6 carbon atoms, a hydroxyl radical or a vinyl radical;

n and p are chosen so as to give the silicone gum a viscosity preferably of greater than 100,000 mPa s, and more preferably of greater than 500,000 mPa s.

In general, n and p may have values preferably ranging from 0 to 5000, and more preferably ranging from 0 to 3000.

As silicone gum which may be used according to (the invention, there may preferably be mentioned those for which:

the substituents R1 to R6 and X represent a methyl group, p=0 and n=2700, such as that sold under the name SE30 by the company General Electric;

the substituents R1 to R6 and X represent a methyl group, p=0 and n=2300, such as that sold under the name AK 500000 by the company Wacker;

the substituents R1 to R6 represent a methyl group, the substituent X represents a hydroxyl group, p=0 and n=2700, in solution at a concentration of 13% in cyclopentasiloxane, such as that sold under the name Q2-1401 by the company Dow Corning;

the substituents R1 to R6 represent a methyl group, the substituent X represents a hydroxyl group, p=0 and n=2700, in solution at a concentration of 13% in polydimethylsiloxane, such as that sold under the name Q2-1403 by the company Dow Corning;

the substituents R1, R2, R5, R6 and X represent a methyl group and the substituents R3 and R4 represent an aryl group and p and n are such that the molecular weight of the compound is 600,000, such as that sold under the name 761 by the company Rhone-Poulenc.

The composition according to the invention preferably also comprises at least one silicone oil, in a proportion preferably ranging from 10 to 90%.

A volatile or non-volatile silicone oil may be used. There may be mentioned, for example:

cyclomethicones D4, D5, D6;

polydimethylsiloxanes (PDMS) of viscosity preferably less than 100 mPa s and more preferably less than 10 mPa s;

alkyldimethicones such as X2-1731 from Dow corning corresponding to the formula:

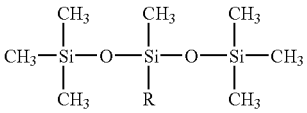

II in which R represents the radical $C_nH_{2n+1}$, with n having a value preferably ranging from 3 to 8. The silicone oil is Preferably present in the composition in a proportion ranging from 30 to 70%.

According to a preferred embodiment of the invention, the silicone oil and gum are used in the form of a homogeneous premix consisting of the silicone gum solubilized in the silicone oil.

The composition according to the invention preferably also comprises pigments, in a proportion ranging from 0.5 to 15%, and more preferably ranging from 2 to 8%.

The pigments may be white or coloured and inorganic or organic.

The pigments used in the composition according to the invention may or may not be coated.

U.S. Pat. No. 4,578,566, the disclosure of which is incorporated herein by reference, describes a pretreatment of pigments in order to make them hydrophobic, as a solution in order to introduce large proportions thereof into silicone-based compositions, and in order to ensure better dispersion thereof in the composition. This pretreatment is carried out by coating the pigments with a polysiloxane. Obviously, this pretreatment increases not only the preparation time of the compositions but also their cost.

As has been mentioned above, a particular advantage of the invention lies in the fact that the compositions according to the invention allow a homogeneous and stable dispersion to be obtained, even when pigments which have not been precoated are used.

Among the pigments which may preferably be used, there may be mentioned, without any limiting effect, titanium dioxide ($TiO_2$), zinc oxide (ZnO), zirconium dioxide ($ZrO_2$), black, yellow, red and brown iron oxides, cerium dioxide ($CeO_2$) or alternatively the organic pigments known as barium, strontium, calcium and aluminium lakes.

The composition according to the invention preferably contains 0 to 30% of fillers. These fillers may preferably be inorganic or synthetic and lamellar or non-lamellar.

Talc, mica, silica, kaolin, powders of nylon and of polyethylene, Telfon, starch, titanium mica, natural mother of pearl, boron nitride and hollow microspheres such as Expancel from Nobel Industrie may be mentioned.

The composition according to the invention may also comprise constituents usually used in cosmetic compositions of this type. These constituents are preferably chosen as a function of the desired cosmetic effect for the final composition, such as the covering power, the transparency, the matt quality and/or the satiny appearance.

There may be mentioned, without any limiting effects:

gelling agents, such as the modified clays known under the name bentone, which are sold by the company NL Industrie and used as they are or prepackaged in a gel; hydrophobic silica; waxes, for example polyethylene; aluminum fatty salts. The percentage of gelling agent in the composition will be chosen depending on whether a supple or creamy formula is desired.

vitamins such as tocopherols and derivatives thereof, vitamin A and derivatives thereof, vitamin C and derivatives thereof such as the fatty esters, including the palpitate ester.

sunscreens such as octyl methoxycinnamate (Parsol MCX), 3-benzophenone (Uvinul M40), and butyl-methoxydibenzoylmethane (Parsol 1789).

oily materials such as plant oils, synthetic esters, lecithin, fragrances and essential oils.

The processes for the manufacture of the compositions according to the invention do not differ in any way from the processes conventionally used in cosmetics and with which those skilled in the art are fully familiar.

The compositions according to the invention may be in the form of a product for making up the skin, such as a foundation, a blusher, an eyeshadow or a lipstick, or even in the form of a hair product such as a styling make-up gel.

Examples of compositions according to the invention will now be given by way of example, without any limiting nature being implied.

EXAMPLE 1

Make-up gels having the following compositions (in g) were prepared:

| | | Compos. A | Compos. B | Compos. C |
|---|---|---|---|---|
| A) | Polydimethylsiloxane at a concentration of 12–14% in cyclopentasiloxane (Q2-1401 from Dow) | 67.50 | 67.50 | 67.50 |
| B) | $TiO_2$ + iron oxides* | 3.36 | 3.36 | 3.36 |
| C) | cyclopentadimethyl-siloxane | 9.50 | 9.50 | — |
| D) | Gelling agent | | | |
| | bentone gel IMP (NL Industrie) | 18.64 | 19.14 | — |
| | bentone gel VS-5 PC (Stearinerie Dubois) | — | 28.14 | 28.14 |
| E) | Fillers | | | |
| | Expancel microspheres | 1.00 | 1.00 | 1.00 |
| | Teflon Ceri-dust | — | 2.00 | — |

*Non-coated pigments

A) and B) were mixed together with a spatula and were passed 3 times through a cylinder mill. C), D) and E) were then added with moderate stirring.

Three formulae were obtained, which contained a large proportion of silicone-containing compounds and which made it possible to obtain, after spreading on the skin, a coloured and water-resistant make-up.

Although the pigments used were not precoated, the pigments were fully dispersed in the composition and the make-up obtained was homogeneous.

EXAMPLE 2

Self-tanning compositions having the following compositions (in g) were prepared:

| | | Compos. D | Compos. E | Compos. F |
|---|---|---|---|---|
| A) | Polydimethylsiloxane at a concentration of 12–14% in cyclopentasiloxane (Q2-1401) | 67.50 | 67.50 | 67.50 |
| B) | $TiO_2$ + iron oxides* | 3.36 | 3.36 | 3.36 |
| C) | Crosslinked silicone powder in a PDMS (KSG 16 from Shin Etsu) | 20.00 | 10.00 | 10.00 |
| | bentone gel VS-5 PC (Dubois) | — | 10.00 | — |
| | Unitwix (United Guardian) | — | — | — |
| D) | Polyvinylidene | 1.00 | 1.00 | 1.00 |
| E) | Silicone oils | | | |
| | Alkyldimethicone X2-1731 (Dow) | — | — | 5.00 |
| | Cyclopentadimethyl-siloxane | qs 100 | qs 100 | qs 100 |

*Non-coated pigments

Thickened gelled creams were obtained, which were easy and pleasant to apply, and which gave a homogeneous and uniform coloration of natural appearance to the skin.

EXAMPLE 3

Water-resistant silicone-containing self-tanning compositions having the following compositions (in g) were prepared:

| | | Compos. G | Compos. H |
|---|---|---|---|
| A) | Silcone oil (AK 500,000 from Wacker) | 10.00 | — |
| | Polydimethylsiloxane at a concentration of 12–14% is cyclomethicone (Q2-1401 from Dow) | 6.64 | 12.30 |
| | Polyphenylsiloxane at a concentration of 15% in cyclopentadimethylsiloxane (Silbione 71634 from Rhone-Poulenc) | — | 40.00 |
| B) | $TiO_2$ + iron oxides* | 3.36 | 7.7 |
| C) | Crosslinked silicone powder (KSG 16 from Shin Etsu) | 20.00 | 10.00 |
| D) | Gelling agent (Bentone gel VS38 from Rhéox) | — | 18.00 |
| E) | Silicone-containing resin beads (Tospearl 120 from Toshiba) | — | 5.00 |
| F) | Cyclopentadimethylsiloxane | 60.00 | qs 100 |

*Non-coated pigments

Coloured and water-resistant self-tanning compositions were obtained in the form of gels.

EXAMPLE 4

A lipstick having the following composition was prepared:

| | |
|---|---|
| Polydimethylsiloxane at a concentration of 12–14% in cyclomethicone (Q2-1401) | 70.00 |
| Crosslinked silicone powder in PDMS (KSG 16 from Shin Etsu) | 10.00 |
| Cyclopentadimethylsiloxane | 10.00 |
| Silicone-coated titanium oxide | 2.83 |
| Silicone-coated iron oxides | 4.70 |
| D&C red No. 7 | 0.47 |
| Titanium mica | 2.00 |

A fluid gelled cream of red-pink colour with an iridescent effect was obtained, which was smooth upon application and had good staying power.

EXAMPLE 5

A screening tanning fluid having the following composition was prepared:

| | |
|---|---|
| Polydimethylsiloxane at a concentration of 12–14% in cyclomethicone (Q2-1401) | 70.00 |
| UV screening agents Parsol MCX from BASF | 7.00 |
| Hydroxy-4-methoxybenzophenone | 2.00 |
| FINSOLV TN ($C_{12}$–$C_{15}$ alkyl benzoate) from Finetax | 9.00 |
| Jojoba oil | 1.00 |
| α-tocopheryl acetate | 1.00 |
| Ethanol | 4.70 |
| Fragrance | 0.30 |
| Crosslinked silicone powder in PDMS (KSG 16 from Shin Etsu) | 10.00 |
| $TiO_2$ + iron oxides (non-coated) | 1.70 |

A shiny, smooth brown-coloured tanning fluid was obtained, which was easy to apply and gave a homogeneous and uniform coloration of natural appearance to the skin.

What is claimed is:

[1. A cosmetic composition comprising from 2% to 50% of at least one silicone gum, from 10% to 90% of at least one silicone oil, from 0.5% to 15% of at least one pigment, and from 0 to 30% of at least one filler, wherein said at least one silicone gum is of the formula:

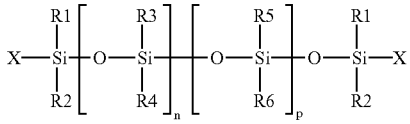

in which

R1, R2, R5 and R6 each independently represents an alkyl radical having from 1 to 6 carbon atoms;

R3 and R4 each independently represents an alkyl radical having from 1 to 6 carbon atoms or an aryl radical;

X represents an alkyl radical having from 1 to 6 carbon atoms, a hydroxyl radical or a vinyl radical; and n and p are selected so as to give said silicone gum a viscosity of greater than 100,000 mPa s, and wherein said composition is anhydrous and water-resistant, and further wherein said composition has cosmetic properties.]

[2. A composition according to claim 1, wherein said at least one silicone gum is present in an amount which ranges from 4% to 15% by weight relative to the total weight of said composition.]

[3. A composition according to claim 2, wherein said at least one silicone gum is present in an amount which ranges from 6% to 9%, by weight relative to the total weight of said composition.]

[4. A composition according to claim 1, wherein n and p have values ranging from 0 to 5000.]

[5. A composition according to claim 4, wherein n and p have values ranging from 0 to 3000.]

[6. A composition according to claim 1, wherein said at least one silicone gum is a gum wherein:

the substituents R1 to R6 and X represent a methyl group, p=0 and n=2700;

the substituents R1 to R6 and X represent a methyl group, p=0 and n=2300;

the substituents R1 to R6 represent a methyl group, the substituent X represents a hydroxyl group, p=0 and n=2700; or the substituents R1, R2, R5, R6 and X represent a methyl group, and the substituents R3 and R4 represent an aryl group, and p and n are selected such that the molecular weight of the compound is approximately 600,000.]

[7. A composition according to claim 1, wherein said at least one silicone oil is present in an amount which ranges from 30% to 70%.]

[8. A composition according to claim 1, wherein said at least silicone oil is a cyclomethicone, a polydimethylsiloxane of viscosity less than 100 mPa s, or an alkyldimethicone.]

[9. A composition according to claim 1, wherein said at least one pigment is present in an amount which ranges from 2 to 8% by weight relative to the total weight of the composition.]

[10. A composition according to claim 1, wherein said at least one pigment is inorganic or organic and is coated or non-coated.]

[11. A composition according to claim 1, wherein said at least one pigment is titanium dioxide, zinc oxide, zirconium dioxide, black, yellow, red or brown iron oxide, cerium dioxide, an organic pigment or a mixture thereof.]

[12. A composition according to claim 11, wherein said organic pigment is barium, strontium, calcium or aluminium lakes.]

[13. A composition according to claim 1, which is in the form of a make-up product or a hair product.]

[14. A composition according to claim 13, wherein said make-up product is a lipstick, a blusher, an eyeshadow or a foundation and said hair product is a styling make-up gel.]

[15. A composition according to claim 1, wherein said at least one silicone gum and said at least one silicone oil are present in the form of a homogeneous premix consisting of said at least one silicone gum solubilized in said at least one silicone oil.]

[16. A composition according to claim 1, wherein said at least one filler is inorganic or synthetic and lamellar or non-lamellar.]

[17. A composition according to claim 1, which further comprises at least one gelling agent, vitamin, sunscreen or oil material.]

*18. A cosmetic composition comprising from 2% to 50% of at least one silicone gum, at least one crosslinked silicone, at least one pigment in an amount ranging from 0.5% to 15%, and at least one gelling agent, wherein said at least one silicone gum is of the formula:*

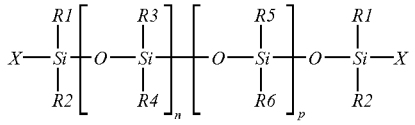

*in which*

*R1, R2, R5 and R6 are each independently chosen from alkyl radicals having from 1 to 6 carbon atoms;*

*R3 and R4 each independently chosen from alkyl radicals having from 1 to 6 carbon atoms and aryl radicals;*

*X is chosen from alkyl radicals having from 1 to 6 carbon atoms, hydroxyl radicals, and vinyl radicals; and*

*n and p are independently chosen so as to give said silicone gum a viscosity of greater than 100,000 mPa•s, and*

*wherein said composition is anhydrous and water-resistant.*

*19. A cosmetic composition according to claim 18, wherein said at least one pigment is chosen from titanium dioxide, zinc oxide, zirconium dioxide, black iron oxide, yellow iron oxide, red iron oxide, brown iron oxide, cerium dioxide, and organic pigments.*

*20. A cosmetic composition according to claim 18, which is in a form chosen from make-up products and hair products.*

*21. A cosmetic composition according to claim 20, wherein said make-up products are chosen from lipsticks, blushers, eyeshadows, and foundations, and said hair products are chosen from styling make-up gels.*

*22. A cosmetic composition according to claim 18 for application to the lips.*

*23. A cosmetic composition according to claim 18 comprising at least one filler in an amount up to 30%, wherein said at least one filler is chosen from talc, mica, silica, kaolin, nylon powders, polyethylene powders, Teflon, starch, titanium mica, natural mother of pearl, boron nitride, and hollow microspheres.*

*24. A cosmetic composition according to claim 18, wherein said at least one crosslinked silicone is chosen from silicone resins.*

*25. A cosmetic composition according to claim 18, wherein, in said at least one silicone gum, R1 to R6 and X are methyl.*

*26. A cosmetic composition according to claim 18, wherein, in said at least one silicone gum, R1 to R6 and X are methyl, and p is 0.*

*27. A cosmetic composition comprising:*

*from 2% to 50% of at least one silicone gum;*

*at least one crosslinked silicone;*

*at least one gelling agent;*

*optionally at least one filler in an amount up to 30%; and*

*at least one pigment in an amount ranging from 0.5% to 15%;*

*wherein said at least one silicone gum is of the formula:*

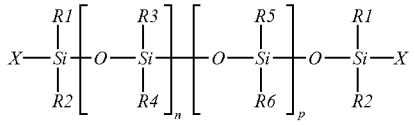

*in which*

*R1, R2, R5 and R6 are each independently chosen from alkyl radicals having from 1 to 6 carbon atoms;*

*R3 and R4 are each independently chosen from alkyl radicals having from 1 to 6 carbon atoms and aryl radicals;*

*X is chosen from alkyl radicals having from 1 to 6 carbon atoms, hydroxyl radicals, and vinyl radicals; and*

*n and p are independently chosen so as to give said silicone gum a viscosity of greater than 100,000 mPa•s, and*

*wherein said cosmetic composition is anhydrous and water-resistant.*

*28. A cosmetic composition according to claim 27, wherein said at least one crosslinked silicone is chosen from silicone resins.*

*29. A cosmetic composition according to claim 27, comprising at least one filler in an amount up to 30%.*

*30. A cosmetic composition according to claim 27, wherein said at least one pigment is chosen from titanium dioxide, zinc oxide, zirconium dioxide, black iron oxide, yellow iron oxide, red iron oxide, brown iron oxide, cerium dioxide, and organic pigments.*

*31. A cosmetic composition according to claim 27, which is in a form chosen from make-up products and hair products.*

*32. A cosmetic composition according to claim 31, wherein said make-up products are chosen from lipsticks, blushers, eyeshadows, and foundations, and said hair products are chosen from styling make-up gels.*

*33. A cosmetic composition comprising:*

*from 2% to 50% of at least one silicone gum;*

*at least one crosslinked silicone;*

*at least one filler in an amount up to 30%; and*

*at least one pigment in an amount ranging from 0.5% to 15%;*

*wherein said at least one silicone gum is of the formula:*

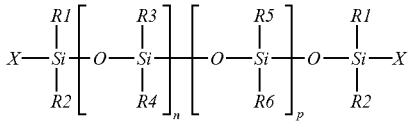

*in which*

*R1, R2, R5 and R6 are each independently chosen from alkyl radicals having from 1 to 6 carbon atoms;*

*R3 and R4 are each independently chosen from alkyl radicals having from 1 to 6 carbon atoms and aryl radicals;*

*X is chosen from alkyl radicals having from 1 to 6 carbon atoms, hydroxyl radicals, and vinyl radicals; and*

*n and p are independently chosen so as to give said silicone gum a viscosity of greater than 100,000 mPa•s, and*

*wherein said cosmetic composition is anhydrous and water-resistant.*

*34. A cosmetic composition according to claim 33, wherein said at least one filler is chosen from talc, mica, silica, kaolin, nylon powders, polyethylene powders, Teflon, starch, titanium mica, natural mother of pearl, boron nitride, and hollow microspheres.*

*35. A cosmetic composition according to claim 33, wherein said at least one crosslinked silicone is chosen from silicone resin.*

*36. A cosmetic composition according to claim 33, wherein said at least one pigment is chosen from titanium dioxide, zinc oxide, zirconium dioxide, black iron oxide, yellow iron oxide, red iron oxide, brown iron oxide, cerium dioxide, and organic pigments.*

*37. A cosmetic composition according to claim 33, which is in a form chosen from make-up products and hair products.*

*38. A cosmetic composition according to claim 37, wherein said make-up products are chosen from lipsticks, blushers, eyeshadows, and foundations, and said hair products are chosen from styling make-up gels.*

*39. A cosmetic composition according to claim 18, further comprising at least one filler in an amount up to 30%.*

*40. A cosmetic composition comprising from 2% to 50% of at least one silicone gum, at least one crosslinked silicone, at least one pigment in an amount ranging from 0.5% to 15%, and at least one modified clay, wherein said at least one silicone gum is of the formula:*

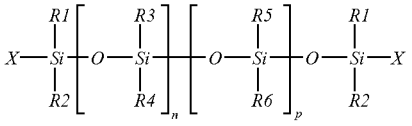

*in which*

*R1, R2, R5 and R6 are each independently chosen from alkyl radicals having from 1 to 6 carbon atoms;*

*R3 and R4 are each independently chosen from alkyl radicals having from 1 to 6 carbon atoms and aryl radicals;*

*X is chosen from alkyl radicals having from 1 to 6 carbon atoms, hydroxyl radicals, and vinyl radicals; and*

*n and p are independently chosen so as to give said silicone gum a viscosity of greater than 100,000 mPa•s, and*

*wherein said cosmetic composition is anhydrous and water-resistant.*

*41. A cosmetic composition comprising:*

*from 2% to 50% of at least one silicone gum;*

*at least one crosslinked silicone;*

*at least one modified clay;*

*optionally at least one filler in an amount up to 30%; and*

*at least one pigment in an amount ranging from 0.5% to 15%;*

*wherein said at least one silicone gum is of the formula:*

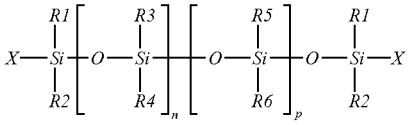

*in which*

*R1, R2, R5 and R6 are each independently chosen from alkyl radicals having from 1 to 6 carbon atoms;*

*R3 and R4 are each independently chosen from alkyl radicals having from 1 to 6 carbon atoms and aryl radicals;*

*X is chosen from alkyl radicals having from 1 to 6 carbon atoms, hydroxyl radicals, and vinyl radicals; and*

*n and p are independently chosen so as to give said silicone gum a viscosity of greater than 100,000 mPa•s, and*

*wherein said cosmetic composition is anhydrous and water-resistant, and*

*wherein said cosmetic composition is a lip composition.*

* * * * *

UNITED STATES PATENT AND TRADEMARK OFFICE

CERTIFICATE OF CORRECTION

PATENT NO. : RE 39,218 E
APPLICATION NO. : 09/987885
DATED : August 1, 2006
INVENTOR(S) : Myriam Mellul et al.

It is certified that error appears in the above-identified patent and that said Letters Patent is hereby corrected as shown below:

Col. 8, line 11, "*R4 each*" should read -- *R4 are each* --.

Col. 9, line 62, "*resin*" should read -- *resins* --.

Signed and Sealed this

Twenty-sixth Day of December, 2006

JON W. DUDAS
*Director of the United States Patent and Trademark Office*